United States Patent
Bloom, Jr. et al.

(10) Patent No.: US 6,414,194 B1
(45) Date of Patent: Jul. 2, 2002

(54) PROCESS AND APPARATUS FOR MAKING ULTRA-PURE DMSO

(75) Inventors: Claude A. Bloom, Jr., Bogalusa, LA (US); Charles G. Ashe, Carriere, MS (US); John L. Ferguson, Bogalusa, LA (US); Joe P. Gibbons, Jr., Diamondhead, MS (US); Kenneth W. Otto, St. Pete Beach, FL (US); Alan M. Rodger, Bogalusa, LA (US)

(73) Assignee: Gaylord Chemical Corporation, Slidell, LA (US)

( * ) Notice: Subject to any disclaimer, the term of this patent is extended or adjusted under 35 U.S.C. 154(b) by 0 days.

(21) Appl. No.: 09/557,237

(22) Filed: Apr. 24, 2000

Related U.S. Application Data (60) Provisional application No. 60/130,740, filed on Apr. 23, 1999, and provisional application No. 60/159,151, filed on Oct. 13, 1999.

(51) Int. Cl.⁷ ............................................. C07C 315/00
(52) U.S. Cl. ......................................................... 568/27
(58) Field of Search ........................................... 568/27

(56) References Cited

U.S. PATENT DOCUMENTS

| | | | |
|---|---|---|---|
| 3,045,051 A | * | 7/1962 | Coma et al. |
| 3,358,037 A | | 12/1967 | Allegretti et al. |
| 3,708,542 A | * | 1/1973 | Douchet et al. |
| 5,090,965 A | * | 2/1992 | Kehm et al. |

FOREIGN PATENT DOCUMENTS

| | | |
|---|---|---|
| DE | 1261502 | 9/1967 |
| FR | 1494966 | 8/1967 |
| FR | 1484173 | 9/1967 |
| JP | 7118223 | 5/1995 |

OTHER PUBLICATIONS

Philippe et al., "Etude critique des dierents modes de purification du dimethylsufoxyde", Bull. Soc. Chem. France No. 11, pp. 4713–4716, 1968(plus English translation).
CA: 133:121980 abs of EP1024136 Aug. 2000.*

* cited by examiner

Primary Examiner—Jean F. Vollano
(74) Attorney, Agent, or Firm—Needle & Rosenberg, P.C.

(57) ABSTRACT

One aspect of this invention relates to processes for solidifying dimethylsufoxide including the steps of partially solidifying a liquid phase including dimethylsulfoxide and one or more impurities, to form a mixture comprising solid dimethylsulfoxide and a liquid residue, and substantially separating the solid dimethylsulfoxide from the liquid residue, wherein the liquid residue comprises liquid dimethylsulfoxide and at least a portion of the impurities, and wherein the liquid residue is not subsequently treated by any step of partial solidification. In certain embodiments of the processes of the invention, ultra-high purity DMSO that exceeds the purity specifications for U.S.P. grade DMSO can be produced by employing solidification, fractional solidification and/or melt crystallization processes.

26 Claims, 3 Drawing Sheets

PROCESS AND APPARATUS FOR MAKING ULTRA-PURE DMSO

CROSS REFERENCE TO RELATED APPLICATIONS

This application claims priority to U.S. Provisional Application Serial No. 60/130,740, filed Apr. 23, 1999, and also claims priority to U.S. Provisional Application Serial No. 60/159,151, filed Oct. 13, 1999, which applications are both hereby incorporated by this reference in their entireties.

BACKGROUND OF THE INVENTION

1. Field of the Invention

The present invention relates to processes for solidifying or crystallizing dimethylsulfoxide, processes for purifying dimethylsulfoxide by melt crystallization, and/or processes for producing ultra-pure dimethylsulfoxide and/or U.S.P. grade dimethylsulfoxide.

2. Background Art

It is known in the art to purify certain chemicals, especially certain organic chemicals, by solidification, fractional solidification, and/or crystallization, to remove impurities from the chemicals. In solidification, fractional solidification and/or crystallization processes, the compound to be purified and the impurities are a component of a liquid medium. A change of conditions(such as removal of a solvent, or a change in temperature) is used to induce the compound to be purified to exceed its solubility in the medium, so as to induce solidification or crystallization. Preferably, the impurities remain substantially in the medium, and the solidified or crystallized compound is therefore purified. Solidification processes may be subdivided into layer processes, wherein solidification occurs on a solid surface, or suspension processes wherein the solid and/or crystals form as a suspension in the liquid medium. The general principals of solidification and/or crystallization are taught in treatises such as: *Principles of Solidification* by Bruce Chalmers (John Wiley & Sons 1964); "Fractional Crystallization", *Process Technology Proceedings, 6, Industrial Crystallization* 87, by S. J. Jancic (Proceedings of the 10th Symposium on Industrial Crystallization, Bechyne, Czechoslovakia, Sep. 21–25, 1987); and *Fractional Solidification,* by Zief et.al. (Marcel Dekker, Inc. 1967); which are hereby incorporated by reference.

It is also known in the art to purify certain chemicals by the technique of "melt crystallization." In melt crystallization, the compound to be purified typically comprises a major fraction, or preferably a high fraction of the mixture to be purified, but nevertheless contains (preferably minor) impurities. Solvents are not typically added to melt crystallization processes. The mixture (which may be a solid at ambient temperature) is maintained at a temperature above its melting point to form a liquid medium, then cooled below the melting point of the compound to be purified, to induce solidification or crystallization out of the "melt". If the solid and/or crystals are removed from the melt before all of the desired compound has crystallized (i.e. the liquid phase is fractionally solidified and/or crystallized), the impurities will concentrate in a liquid melt residue, that can be readily separated from the solid or crystals. The purity of crystals formed by melt crystallization processes can be very good. The general techniques and methods employed in melt crystallization have been discussed in treatises by Sloan et al., in "Techniques of Melt Crystallization", *Techniques of Chemistry*, vol. XIX (John Wiley & Sons, 1988); by Wynn in "Melt Crystallization" in Section 5.3 of *Handbook of Separation Techniques for Chemical Engineers*, 3d ed., (P. A. Scheitzer Ed., McGraw-Hill 1997), and by Toyokura et al., in "Crystallization from the Melt", *Crystallization Technology Handbook,* (Marcel Dekker, Inc. 1995), which are hereby incorporated by reference in their entireties.

Purification of a compound by melt crystallization tends to be somewhat more expensive than alternative purification methods such as distillation. Nevertheless, melt crystallization is sometimes applied to purify compounds that are stable at the temperature of their "melt", but exhibit objectionable chemical reactivity or thermal instability when distilled, as illustrated by the process for preparing acrylic acid derivatives disclosed in U.S. Pat. No. 5,831,124. An example the application of a melt crystallization process to the purification of 1,4-butanediol was recently disclosed in U.S. Pat. No. 5,981,810. The above-described patents are hereby incorporated by reference in their entireties, for their disclosure of generally known industrial methods and apparatus suitable for melt crystallization processes.

Dimethylsulfoxide, $CH_3-S(O)-CH_3$, (which may alternatively be termed dimethyl sulfoxide, methyl sulfoxide, sulfinylbis[methane], or "DMSO") is an excellent solvent, and is employed in many diverse commercial applications. Commercial grades of DMSO that are available in bulk quantities have a variety of purity levels. "Industrial" grade DMSO typically has a purity of greater than about 99.7% by weight, can be readily and economically prepared by distillation processes, and is suitable for many of the industrial applications of DMSO. Higher purity grades of DMSO (up to about 99.995% DMSO) are available, and can be prepared by more complex distillation techniques.

Nevertheless, there are applications wherein yet higher purity DMSO, i.e., "ultra-high purity DMSO," would be desirable, especially pharmaceutical applications. For example, if DMSO is present in a pharmaceutical composition at a concentration of greater than about 70 percent by weight, it is known that DMSO can induce the penetration of human or animal skin by other components of the composition, including many pharmaceutical agents. The DMSO also penetrates human or animal skin at such high concentrations, but because DMSO is very non-toxic, known pharmaceutical formulations have employed DMSO as a carrier or vehicle for administering the pharmaceutical agents. Nevertheless, the ability of DMSO to aid the skin penetration of other materials raises concerns about potentially toxic impurities in the DMSO. Therefore, the United States Pharmacopeia has defined specifications for "U.S.P. grade" DMSO of very high purity Among other requirements, U.S.P. grade DMSO has a maximum of 0.1 % impurities by weight, and must satisfy several other specifications, including very low levels of absorption of ultraviolet light.

Economical production of DMSO of such high purity is unexpectedly technically difficult and expensive when prior art methods of purification are employed. In particular, distillation of DMSO by normal methods results in the formation of trace impurities that absorb ultraviolet light at levels in excess of the levels permitted by the U.S.P. specifications. As a result, DMSO that meets or exceeds the U.S.P. grade specifications is not commercially available. Thus, there is a need in the art for ultra-high purity DMSO that exceeds U.S.P. specifications, and improved methods for its production.

SUMMARY OF THE INVENTION

Applicants have discovered that DMSO may be readily purified by solidification, fractional solidification and/or melt crystallization processes. Through processes that employ such techniques, DMSO can (if desired) be produced in surprisingly high purity. In fact, ultra-high purity DMSO that exceeds the purity specifications for U.S.P. grade DMSO can be produced by employing solidification, fractional solidification and/or melt crystallization processes. This invention, however, is not limited to the production of high purity or ultra-high purity DMSO.

One aspect of this invention relates to processes for solidifying dimethylsufoxide including the steps of partially solidifying a liquid phase including dimethylsulfoxide and one or more impurities, to form a mixture comprising solid dimethylsulfoxide and a liquid residue, and substantially separating the solid dimethylsulfoxide from the liquid residue, wherein the liquid residue comprises liquid dimethylsulfoxide and at least a portion of the impurities. The inventive processes do not include processes wherein the liquid residue is recycled and subsequently treated by the partial solidification step.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate a preferred embodiment of an apparatus that may be employed in the practices of the processes of the invention, and together with the description, serve to explain the principles of the invention.

DETAILED DESCRIPTION OF THE INVENTION

The present invention may be understood more readily by reference to the following detailed description of preferred embodiments of the invention and the Examples included therein and to the Figures and their previous and following description.

Before the present compositions and methods are disclosed and described, it is to be understood that this invention is not limited to any specific apparatus for carrying out the methods of the invention, unless so stated in the claims, as the apparatus may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an impurity" includes mixtures of impurities, and reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. For example, the phrase "optional cooling coil" means that a cooling coil may or may not be present in the indicated apparatus.

Reference will now be made in detail to the present preferred embodiment(s) of the invention. Wherever possible, the same reference numbers are used throughout the drawings to refer to the same or like parts.

In one aspect, the invention includes a process for solidifying dimethylsufoxide, comprising one or more repetitions of the steps of:

a. providing a liquid phase comprising dimethylsulfoxide and one or more impurities, b. partially solidifying the liquid phase to form a mixture comprising solid dimethylsulfoxide and a liquid residue, wherein the liquid residue comprises liquid dimethylsulfoxide and at least a portion of the impurities, and c. substantially separating the solid dimethylsulfoxide from the liquid residue.

In preferred embodiments, the solidification and/or crystallization processes of the invention optionally further comprises the step of:

d. collecting the solid dimethylsulfoxide to provide purified dimethylsulfoxide.

The solidification and/or crystallization processes of the instant invention may be practiced continuously, semi-continuously, or in a stepwise manner. In a continuous process, steps a, b, c and/or d may occur simultaneously. A continuous process comprising one or more stages of solidification might be arranged in series or in parallel, wherein each stage comprises steps a, b, c, and/or d. The process may also be conducted in a stepwise manner, as for example in batch processes, wherein each of the steps might be readily and separately identifiable. The steps of the instant processes may occur in any order, or number of substages. For example, step a might be followed by one or more repetitions of steps b and/or c, then followed by an additional repetition of steps a, b, and/or c and then followed by step d. In preferred batch processes, steps a, b, c, and optionally step d occur in the indicated order. The processes may also be practiced semi-continuously, the process having both continuous and stepwise features.

The solidification and/or crystallization processes may comprise one or more repetitions of steps a, b, and c, and optional step d. It is to be understood that solid DMSO produced by an initial repetition of the steps of the process may optionally be subjected to a subsequent solidification, crystallization, or melt crystallization process, to provide DMSO of further increased purity. In a subsequent solidification, crystallization, or melt crystallization process, the solid or purified DMSO produced by a first repetition of the steps a, b, c, and/or d is collected, melted, dissolved in, and/or otherwise converted to a liquid phase, then subjected to one or more subsequent solidification, crystallization, or melt crystallization processes. The one or more subsequent solidification, crystallization, or melt crystallization processes may, but need not, comprise a repetition of the steps of the initial process. Preferably, the subsequent repetitions of a solidification, crystallization, or melt crystallization process comprises steps a, b, and c, and optionally step d. It also is to be understood that the liquid phase provided to subsequent solidification, crystallization, or melt crystallization processes may comprise either solid, or purified DMSO, and/or liquid residue from a previous repetition of a solidification, crystallization, or melt crystallization process.

Nevertheless, in certain preferred embodiments, the initial liquid phase is only subjected to a single repetition of the steps, and therefore consists essentially of steps a, b, c, and optionally step d. Stated alternatively, in some embodiments, solid DMSO produced by an initial repetition of the steps of the process may preferably not be further subjected to steps a, b, c, and or d. A process using a single repetition of the steps can be economically desirable, and can be effective in purifying liquid phases that are already of reasonably high purity.

The liquid phase provided in step a of the process comprises dimethylsulfoxide and one or more impurities. The identity and/or nature of the impurities will of course vary with the purity of and source of the liquid phase. Dimethylsulfone, methyl mercaptan, dimethyldisulfide, methylethylsulfoxide, methyl acetate, and/or dimethylsulfide are common impurities in commercially available DMSO. Additional impurities, such as acidic and basic materials, and a variety of unidentified impurities may also be present. In particular, small quantities of currently unidentified impurities that unacceptably absorb ultraviolet absorption may be produced by prior art processes for the purification of DMSO, such as distillation processes, and those impurities are often present in the liquid phase provided to the current processes. Therefore, the liquid phase may comprise any source of DMSO that has ultraviolet absorbance characteristics greater than the maximum ultraviolet absorbance characteristics allowed by the specifications for U.S.P. grade dimethylsulfoxide.

In some embodiments of the solidification and/or crystallization processes, materials other than DMSO, such as additives or solvents, may be present in or purposely added to the liquid phase. Preferred solvents for such processes include relatively nonpolar solvents, including hydrocarbon solvents, that have significant but limited capacity to dissolve DMSO. In such embodiments, DMSO content of the liquid phase may be low.

In many embodiments, the liquid phase provided to the process is maintained under a blanket of a dry inert gas (such as $N_2$, $CO_2$, and the like), in order to exclude undesirable absorption of water from the atmosphere into the DMSO. The $N_2$ may be added in the form of liquid $N_2$, and the $CO_2$ may be added in the form of dry ice, so as to simultaneously provide desirable cooling and agitation associated with the formation of gas bubbles.

In many preferred embodiments of the solidification processes, the DMSO content of the liquid phase is relatively high, and no additional additives or solvents are added to the liquid phase. The temperature of the liquid phase of many such processes will initially be above the melting point of pure DMSO, then be lowered so as to approach the melting point of DMSO, so that the liquid phase contains "molten" DMSO. Such embodiments of solidification, fractional crystallization and/or crystallization processes may be optionally be termed "melt crystallization processes." Such processes may be employed to purify crude DMSO process streams from a production plant or DMSO streams from a DMSO recycling process.

Preferably the liquid phase comprises at least about 90% dimethylsulfoxide by weight. In more preferred embodiments of the invention, the liquid phase may have higher percentages of DMSO by weight, such as 95, 98, or 99 weight percent. Commercially available grades of DMSO (other than U.S.P. grade dimethylsulfoxide) may also be further purified, including industrial grade comprising higher than about 99.7 weight percent DMSO, ACS grade comprising higher than about 99.9 weight percent DMSO, and pharmaceutical grades of DMSO grade comprising higher than about 99.98 or 99.995 weight percent DMSO.

Step b of the above-outlined process comprises partially solidifying the liquid phase to form a mixture containing solid dimethylsulfoxide and a liquid residue. The solid DMSO may comprise one or more amorphous phases, wherein the DMSO molecules therein exhibit relatively little order in their three dimensional orientations. Preferably the solid DMSO formed comprises at least some crystals or crystalline phases, wherein the DMSO molecules are predominantly arranged in a three-dimensionally ordered form. Therefore, step b may further comprise crystallizing. Crystalline phases often contain relatively low levels of impurities. In practice, the solid DMSO produced by the present solidification and/or crystallization processes often includes a mixture of amorphous and crystalline phases.

Complete solidification of the liquid phase in step b would occlude substantially all the impurities, and provide no purification of the solid DMSO. In contrast, the present processes employ a partial solidification of the liquid phase to produce a liquid residue containing dimethylsulfoxide and at least a portion of the impurities. Preferably, partial solidification will exclude a substantial portion of the impurities from the solid DMSO, which means that the proportion of at least one of the impurities in the solid DMSO will be lower than the proportion of the at least one impurity in the liquid phase and/or liquid residue. The result of excluding a substantial proportion of the impurities from the solid phase will be a purification of the solid DMSO, and a corresponding partitioning or concentration of the impurities excluded from the solid phase into the liquid residue. Even more preferably, partial solidification will exclude a predominant portion of at least one impurity from the solid DMSO, meaning that at least a major portion of the at least one impurity initially present in the liquid phase will be excluded from the solid DMSO, and be partitioned or concentrated in the liquid residue.

In certain embodiments of the solidification and/or crystallization processes of the invention, the solid dimethylsulfoxide formed in step b, or separated in step c comprises from about 1% to about 80% by weight of the liquid phase provided. In some embodiments of the instant solidification processes, low production costs and high recovery of the DMSO is more important than the attainment of ultra-high purity of the DMSO. In such embodiments, the proportion of solid DMSO formed or separated in steps b and/or c will preferably be relatively high, preferably from about 51% to about 70% by weight of the liquid phase provided.

In other embodiments of the processes of the invention, attainment of ultra-high purity in the solid or purified DMSO is more important than high DMSO recovery or increases in production costs. Moreover, in most embodiments of the solidification and/or crystallization processes of the invention, solid DMSO formed earlier in the solidification process tends to be purer than solid DMSO formed later in the process, because of the concentration of impurities in the liquid residue increases as the solidification process proceeds. Therefore, terminating step b of the process at a relatively low percentage of DMSO solidification can have beneficial effects on DMSO quality. "Early" termination of step b also typically decreases process cycle times. Therefore in some preferred embodiments, the mixture of step b comprises a minor quantity of solid dimethylsulfoxide and a major quantity of liquid residue. In other preferred embodiments, the solid dimethylsulfoxide formed or separated may comprise from about 7% to about 50% by weight, or from about 10% to about 30% by weight of the liquid phase provided.

In many embodiments of the processes of the invention, step b further comprises cooling the liquid phase to a temperature effective to form solid dimethylsulfoxide. The melting point of high purity DMSO crystals is about 18.5° C. (65° F.), so that the cooling of the liquid phase will generally be conducted so as to approach a temperature of about 18.5° C., or somewhat lower. The temperature required to form solid dimethylsulfoxide will typically be lower for liquid phases containing relatively higher proportions of other materials, such as impurities. The cooling may be achieved by most means or apparatus known to those of skill in the art for cooling liquid phases, as will be further described hereinbelow.

In many embodiments of the processes of the invention, particularly embodiments comprising melt crystallization, step b further comprises agitating the liquid phase. In solidification or crystallization processes, impurities tend to be excluded from the growing crystal surfaces, and as a result tend to concentrate in a thin liquid layer in contact with and/or immediately adjacent the crystal surfaces. As a result, the impurities may locally concentrate near the crystal surface to a level significantly higher than the concentration of impurities in the bulk of the liquid residue. High local concentrations of impurities can result in undesirable incorporation of relatively high concentrations of the impurities in later formed layers of the solid DMSO surface. Such an undesirable result can be avoided by slowing the rate of crystallization and/or cooling, in order to allow for natural diffusion of the impurities away from the surface, but such an approach adversely effects the rate and productivity of the solidification process. While not wishing to be bound by theory, it is believed that agitation of the liquid phase during step b of the instant processes tends to physically decrease the thickness of the boundary liquid layer, and thereby facilitate the diffusion of the impurities out of the boundary liquid layer and away from the growing solid surfaces. As a result of agitation, the crystallization processes of the present invention can be conducted at high rates, yet maintain high purity in the solid and/or crystals formed.

The agitation of the liquid phase during step b can be carried out by many methods and/or means known to those of skill in the art for mixing liquids. Such methods and/or means include stirrers, mixers (dynamic and static), impellers, pulsing of the liquid, pump around loops, falling film arrangements, bubbling inert gases through the liquid phase, and the like.

Step c of the processes of the invention involves substantially separating the solid dimethylsulfoxide from the liquid residue. The separation of the solid DMSO from the liquid residue may occur by a variety of methods known to those of skill in the art for separating solids and liquids. The separation may comprise removing the liquid residue from fluid contact with the solid dimethylsulfoxide by draining, pumping, filtering, centrifuging and the like. The separation may also comprise removing the solid dimethylsulfoxide from the liquid residue, as exemplified by physical removal of a surface having solid DMSO adhered thereon from the liquid residue, filtration, and the like. The solid DMSO is substantially separated, but need not be totally separated from the liquid residue, and some of the liquid residue may remain entrained with, or remain adhered to the surfaces of the solid DMSO. Preferably, a substantial proportion, or a major portion of the liquid residue is separated from fluid contact with the solid dimethylsulfoxide. More preferably, substantially all of the liquid residue is separated from fluid contact with the solid dimethylsulfoxide.

One method of substantially separating the solid DMSO and the liquid residue comprises "sweating" the solid dimethylsulfoxide. In this method, the liquid residue adhered to the solid DMSO surfaces (that may have locally high concentrations of impurities) is removed by heating the separated solid dimethylsulfoxide to form at least a portion of additional liquid residue, and substantially separating the additional liquid residue from the remaining solid dimethylsulfoxide. The additional liquid residue formed by sweating tends to wash away the adhered liquid residue, and is easily separated from the remaining solid DMSO. A step comprising sweating the solid DMSO is preferably employed when DMSO of ultra-high purity is desired. Nevertheless, in at least some embodiments of the invention sweating is not required to produce ultra-high purity DMSO, or U.S.P. grade DMSO. Sweating adversely affects both the yield and production rate of purified dimethylsulfoxide. Therefore, in some highly preferred embodiments of the solidification processes of the invention do not comprise sweating.

The product of the solidification processes of the invention is solid DMSO. Many embodiments of the invention comprise the optional step d, collecting the solid dimethylsulfoxide to provide purified dimethylsulfoxide. In preferred embodiments of the invention, the solid DMSO produced by steps b and/or c contains lower levels of impurities than the liquid phase and/or the liquid residue. Therefore, collection of the solid DMSO, provides purified DMSO. A wide variety of methods known to those of skill in the art could be employed to collect the solid DMSO. A preferred method for collecting the solid DMSO comprises "melting" i.e., a step of heating the solid dimethylsulfoxide to provide liquid dimethylsulfoxide.

It is to be understood that the above-described alternatives for the extent of DMSO solidification, methods of cooling, methods of agitating, methods of separating, etc may be combined in various ways. Those skilled in the art will appreciate that the selection of preferred processes, and optimization of rates for cooling, agitating, and other process variables are inter-related with the choices of apparatus employed, the desired yield, quality, and production rate, and many other factors. Optimization of the inter-relationships between such process variables is within the level of average skill in the art in many cases.

The purified DMSO may be used for a variety of purposes. DMSO may be purified by solidification from a process stream, and used as feed for another process stream. The purified DMSO may be used as a high purity solvent for industrial processes, including electronics manufacture, pharmaceutical manufacture, and the like. In highly preferred embodiments, the purified dimethylsulfoxide is in a form suitable for administration to the bodies of living animals or humans. The ultra-high purity DMSO provided by the processes of the invention can serve as all or part of a carrier formulation for pharmaceutical agents. The United States Pharmacopoeia has recently defined specifications for "U.S.P. grade" DMSO. Distillation may be employed to produce DMSO that meets many of the requirements. Nevertheless, U.S.P. grade DMSO must have very low levels of absorption of ultraviolet light. Applicants have discovered that production of U.S.P. grade DMSO that meets the requirements for absorption of ultraviolet light is extremely difficult and/or expensive when distillation processes are employed.

Applicants have unexpectedly discovered that the solidification and/or crystallization processes of the current invention can provide purified dimethylsulfoxide having properties that satisfy the specifications for U.S.P. grade dimethylsulfoxide. In particular, the solidification and/or crystallization processes of the invention are particularly effective for removing traces of impurities that are formed during distillation of DMSO, and absorb ultraviolet light having specified wavelengths from about 275 to about 295 nanometers (or at 350 nanometers after treatment of the DMSO with base). Therefore, in certain highly preferred embodiments, the solid dimethylsulfoxide and /or purified dimethylsulfoxide produced by the processes of the invention have ultraviolet absorbance characteristics that satisfy the specifications for U.S.P. grade dimethylsulfoxide. The U.S.P. specifications for dimethylsulfoxide, which may be found in the 1999 U.S. Pharmacopoeia (USP 24, NF19, pages 579–580) are hereby incorporated by reference, for the purpose of defining the U.S.P. specifications and the analytical methods to be employed in determining compliance with the U.S.P. specifications.

The liquid residue formed in step b, and separated in step c of the processes of the present invention typically contain dimethylsulfoxide. If not further treated or recycled, the DMSO in the liquid residue can represent an economically substantial loss of the DMSO provided to the processes. Therefore, the instant invention provides a variety of methods for reclaiming and/or recycling the value of the DMSO in the liquid residues.

Recycling of liquid residues by subsequent solidification processes, to increase product yield, is a technique employed in certain known industrial melt crystallization processes for purifying other compounds. Nevertheless, the purity of such "recycled" DMSO is typically lower than that produced by a preceding repetition of steps a, b, c, and/or d.

The inventive process does not include recycle of liquid residue to the extent that it results in reclamation of the liquid residue by a solidification or crystallization step b.

The invention nevertheless provides alternative methods for reclaiming the DMSO in the liquid residues. In one embodiment the liquid residue is reclaimed by addition to a process for the production of dimethylsulfoxide, which process does not include the step of solidifying dimethylsulfoxide to produce purified dimethylsulfoxide. Such processes for the production of DMSO may comprise normal laboratory or industrial processes for the production or recycling of DMSO, such as distillation. Such processes typically produce lower grades of DMSO, such as industrial grade DMSO, or ACS grade DMSO. Therefore, in some embodiments, the liquid residue produced by the solidification and/or crystallization processes of the present invention is reclaimed by distillation. Because processes for the purification of DMSO that employ only distillation and do not employ partial solidification typically produce unacceptable contamination by impurities that absorb ultraviolet radiation, those processes for the production of dimethylsulfoxide do not typically produce U.S.P. grade dimethylsulfoxide.

In some embodiments of the solidification and/or crystallization processes of the invention, the value of the solid DMSO and/or purified DMSO produced may be high, and the value of the DMSO in the liquid residue may be sufficiently low that reclamation of the liquid residues may not be economically justified. Therefore, in some embodiments of the processes of the invention, the liquid residue may be discarded as waste. In other embodiments of the processes of the invention, the quality of the liquid residues may be very good, and the liquid residue may be sold, or used in non-U.S.P. applications, without further treatment or purification.

An alternative embodiment of the invention provides a process for purifying dimethylsulfoxide by melt crystallization, comprising the steps of:

a. providing a liquid phase comprising greater than about 90% by weight of liquid dimethylsulfoxide, and one or more impurities, b. agitating and cooling the liquid phase to approach a temperature of about 18.5° C. or lower, to form a mixture of solid dimethylsulfoxide and a liquid residue, wherein the liquid residue comprises liquid dimethylsulfoxide and a substantial portion of the impurities, c. substantially separating the solid dimethylsulfoxide from the liquid residue, and d. melting the solid dimethylsulfoxide to provide purified dimethylsulfoxide, wherein:
  i. the liquid residue is not recycled to the extent it results in treatment of the liquid residue by step b,
  ii. the purified dimethylsulfoxide from step d is not further subjected to steps a, b, and c, and
  iii. the purified dimethylsulfoxide has properties that satisfy the specifications for U.S.P. grade dimethylsulfoxide.

The process for melt crystallizing DMSO described immediately above is in many aspects a "non-traditional" process for melt crystallization, specially adapted for economical production of ultra-high purity DMSO. The liquid phase may comprise a process stream from a commercial plant for producing DMSO. Preferred liquid phases are DMSO equivalent to commercially available grades of DMSO that are less pure than U.S.P. grade DMSO. The proportion of solid DMSO separated from the liquid residue may be high or low, but is preferably relatively low, for example, from about 7% to about 50%, or from about 10% to about 30% by weight of the liquid phase provided. When the proportion of solid DMSO separated from the liquid phase is low, the purity of the solid dimethylsulfoxide produced is typically excellent after a single repetition of steps a, b, c, and d, and typically need not be subjected to a subsequent solidification process. The separated solid DMSO may or may not be subjected to a "sweating" process, but sweating is not typically necessary, and therefore does not increase the complexity of the process or increase production cycle times.

When the proportion of solid DMSO separated from the liquid residue is low, little concentration of impurities is observed in the liquid residues formed, and such liquid residues are often acceptable for direct sale as a lower grade of DMSO, or recycled to a different non-melt crystallization process for producing or recycling DMSO, such as an existing distillation process. Moreover, the value of the U.S.P. grade DMSO can be very high in relation to the value of commonly commercially available grades of DMSO, so that the liquid residues may be economically discarded or treated as waste if desired. Such a process can be conducted in an extremely simple and unspecialized apparatus (as will be described hereinbelow) using very few process steps, resulting in low capital and operating costs.

The quality of the purified dimethylsulfoxide produced by the melt crystallization processes of the invention is superior. The quality of the purified dimethylsulfoxide produced by certain preferred embodiments of the invention is believed to be higher than that of any DMSO currently commercially available. Moreover, the purified DMSO is believed to be unique in its lack of ultraviolet light absorbing impurities.

The apparatus employed to carry out the various processes of the invention may be complex, specialized and expensive, or they may be extremely simple and inexpensive, depending on the embodiment of the process to be practiced. In general, the apparatus employed may comprise any chamber or vessel capable of containing the liquid phase therein, and having suitable means for separating the solid dimethylsulfoxide from the liquid residue. Such an apparatus could be as simple as a laboratory flask or vessel having an opening for adding the liquid phase and draining the liquid residue, in combination with means for heating and/or cooling the flask or vessel. In preferred embodiments of solidification and/or melt crystallization processes of the invention, the solidifying step b occurs in a solidification apparatus, which may preferably be adapted with any of various means to improve the efficiency of the processes as described hereinbelow.

Preferably, the solidification apparatus employed in the solidification and/or melt crystallization processes of the invention is a melt-crystallization apparatus, which may carry our dynamic or static methods of melt crystallization. A wide variety of apparatus for melt crystallization are available, or are disclosed by the treatises and/or patents incorporated by reference hereinabove. Suitable apparatus can comprise continuous or batch apparatus having recirculating loops, or stirred tanks. Some melt crystallization apparatus pump liquid phases upward through tubes or chambers which comprise the crystallization surface. In other equipment, an endless belt or conveyor transports the feed material from a crystallization chamber to a melt chamber. Internally cooled plates can be dipped into a melt and removed when the desired quantity of solid has formed on the plate surfaces. Suspension crystallizers form crystals in the melt rather than on cooled surfaces, and recover the crystals by filtration or centrifugation. In certain column crystallizers crystals formed descend by gravity into a melting zone. Zone melting apparatus, in which a melted zone is moved along the length of an elongated volume of the solid, allowing solidification to occur behind the melted zone may also be employed . Most, if not all, known methods for melt crystallization, and most, if not all commercially available apparatus for melt crystallization (such as the various apparatus sold by Sulzer Chemtech A. G. of Winterthur Switzerland) are suitable for practicing the methods of the present invention.

Nevertheless, many embodiments of the solidification and/or melt crystallization processes of the invention may be carried out in a solidification apparatus comprising:

a. at least one vessel adapted for solidifying the liquid phase, b. means for agitating the liquid phase, and c. means for changing the temperature of the liquid phase.

Suitable vessels include any hollow flasks, tanks, reactors, tubes, pipes, lines or the like capable of containing the liquid phase therein. Preferably, the vessel has at least one outlet for adding and/or removing the liquid phase, liquid dimethylsulfoxide, solid dimethylsulfoxide, and/or the liquid residue from the vessel. Solidification may occur substantially in the liquid phase, to provide a suspension of solid DMSO. Preferably the vessel has at least one surface suitable for solidifying dimethylsulfoxide thereon. In some embodiments, the apparatus comprises a vessel wall or baffle, which may be optionally in contact with or connected to a heat transfer element. The heat transfer element may supply heat from electrical sources, direct heating by heated gases, such as steam, hot air, or any other reasonable source of heat. The heat transfer element may supply cooling provided by cold water or air, a chiller, a refrigeration unit, an evaporation unit, or the like. In one preferred embodiment, the heat transfer element is a jacket for the vessel wall, connected to an external supply of heating and/or cooling fluid. The heating and/or cooling fluid may comprise air, water, steam, organic compounds including hydrocarbon oils or alcohols such as ethylene glycol, propylene glycol, or a mixture thereof. Water, propylene glycol, or a mixture thereof is a preferred heating and/or cooling fluid, because of their low toxicity. In other embodiments, the surface comprises a hollow chamber within the vessel, the hollow chamber having inlet and outlet connections to an external supply of heating and/or cooling fluid. Examples of such hollow chambers include hollow baffles, tubes, cooling coils and the like.

Most means for agitating the liquid phase known to those of skill in the art may be suitable, so long as the means for agitating induces reasonably controlled physical movement of the liquid comprising the liquid phase. Examples of suitable means for agitating the liquid phase include stirrers, mixers (dynamic and static), impellers, pulsing of the liquid, bubbling of gases through the liquid phase, pump around loops, falling film arrangements, and the like. In certain preferred embodiments of the means for the means for agitating the liquid phase is an external loop for circulation of liquid dimethylsulfoxide and/or dimethylsulfoxide-containing liquid residue.

Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE 1

Figure 1:
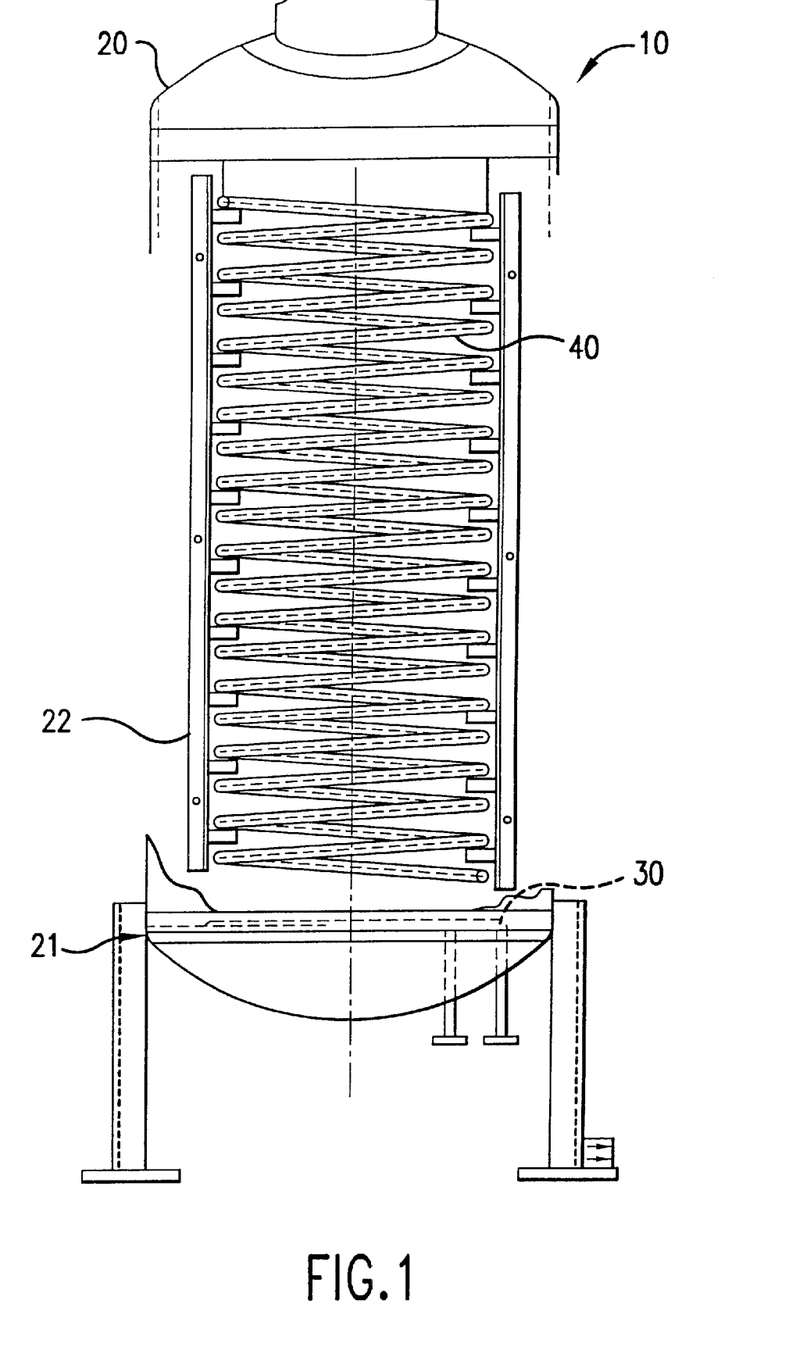
FIG. 1 is a side, cut-away view of a preferred embodiment of a melt crystallization apparatus of the present invention.
Figure 2:
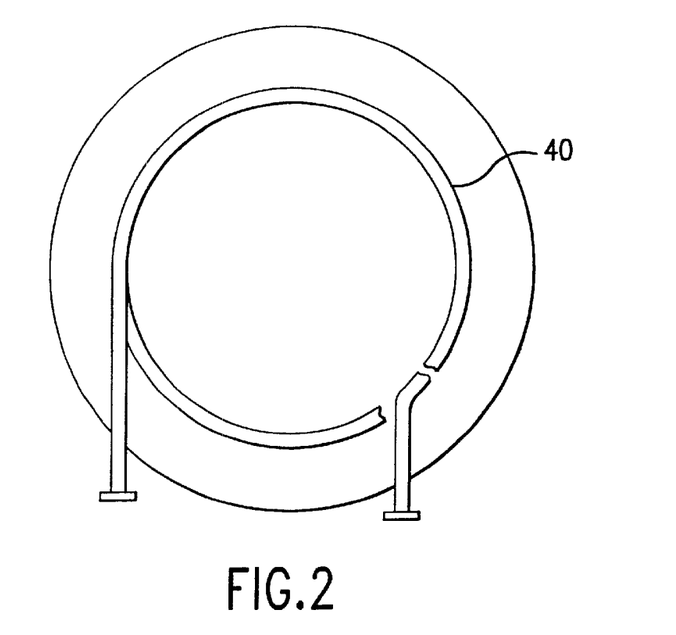
FIG. 2 (view C—C) is a top view of a helical heat exchange coil used in the melt crystallization apparatus of FIG. 1.
Figure 3:
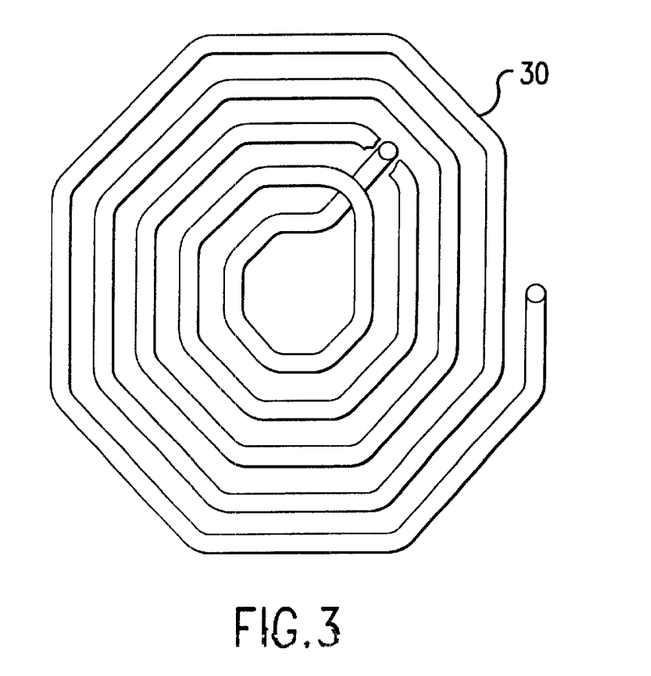
FIG. 3 (view B—B) is a top view of a heat exchange coil used in the melt crystallization apparatus of FIG. 1.
Figure 4:
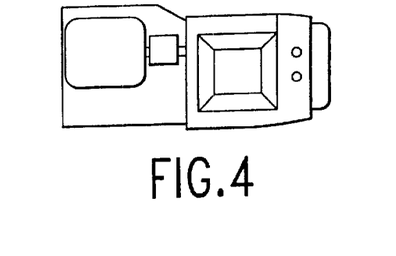
FIG. 4 is a top view of agitation means used in the melt crystallization apparatus of FIG. 1.
Figure 5:
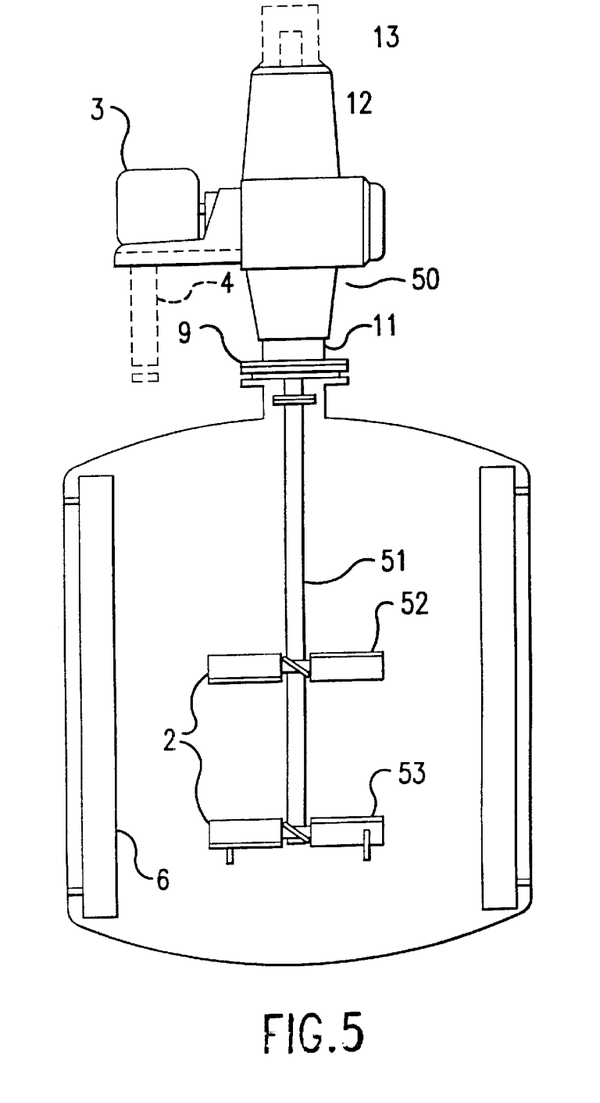
FIG. 5 is a side view of agitation means used in the melt crystallization apparatus of FIG. 1.

FIG. 1 is a cutaway drawing showing a melt crystallization apparatus 10, representative of one preferred embodiment of the present invention. Melt crystallization apparatus 10 includes a vessel 20 which includes a lower heat exchange zone 21 and an upper heat exchange zone 22. Received in the lower heat exchange zone 21 of vessel 20 is a heat exchange coil 30 (shown in FIG. 5) for cooling the liquid phase so that DMSO crystallizes on the coil, and for heating the crystallized DMSO to melt it. Received in the upper heat exchange zone 22 of vessel 20 is a heat exchange coil 40 for cooling the liquid phase so that DMSO crystallizes, and for heating crystallized DMSO to melt it.

An agitating means, agitator 50, includes an impeller 51 including two impeller blade sets 52, 53 positioned in the upper heat exchange zone 22 near the boundary of the upper heat exchange zone 22 and the lower heat exchange zone 21.

In operation, a first quantity of industrial-grade DMSO (99.7% or higher DMSO, for example) is taken from a stock of industrial-grade DMSO (such as that produced by Gaylord Chemical Corporation in Bogalusa, La.). The first quantity is transferred into vessel 20 via an opening in the upper zone of vessel 20. The first quantity is cooled, preferably by circulating a mixture of water and 30% propylene glycol at about 30–50° F. (−1.1–10° C.), and more preferably about 40° F., (4.4° C.) through coils 40 and 30 in upper heat exchange zone 22 and lower heat exchange zone 21, and preferably while the DMSO is being agitated by stirring, until 10–80% of the first quantity crystallizes (primarily onto coils 30 and 40). The portion of the first quantity other than the crystallized DMSO is removed from vessel 20 via an outlet (not shown, but it could be, for example, a 6" nozzle at the bottom of vessel 20). Then, the crystallized DMSO is removed from the melt crystallization apparatus 10 by melting it, preferably by circulating a mixture of water and 30% propylene glycol at about 90–110° F. (32.2–43.3° C.) or higher, (and more preferably about 105° F., 40.5° C.) through coils 40 and 30 (the fluid can travel from one coil into the other coil, for example) in upper heat exchange zone 22 and lower heat exchange zone 21, and allowing the melted product to exit vessel 20 via the outlet. The portion of the first quantity other than the crystallized DMSO is returned to the stock of industrial grade DMSO.

Alternatively, the crystallized DMSO could be melted by using melted purified DMSO as a heat exchange fluid in direct contact with the crystallized DMSO.

The melting point of DMSO is about 65° F. (18.5° C.). The industrial-grade DMSO typically comes in at about 90° F. (32.2° C.). When vessel 20 has the dimensions shown in the attached drawings, it is believed that it will take less than about 16 hours to crystallize a desired quantity of DMSO from it when the heat exchange fluid is as specified herein and has a temperature of about 40° F. (4.4 ° C. Preferably, the process conditions (volume and temperature of heat exchange fluid, for example) are manipulated such that a desired quantity of DMSO crystallizes out in less than 12 hours. Even more preferably, the process conditions are manipulated such that a desired quantity of DMSO crystallizes out in less than 8 hours. Likewise, it is believed that it will take less than about 8 hours to melt a desired crystallized quantity of DMSO when the heat exchange fluid is as specified herein and has a temperature of about 105° F. (40.5° C.). If the heat exchange fluid is too hot the DMSO quality might degrade. Preferably, the process conditions are manipulated such that a desired quantity of crystallized DMSO melts in less than 6 hours. Even more preferably, the process conditions are manipulated such that a desired quantity of crystallized DMSO melts in less than 4 hours.

The freeze time and melt time can be shortened by jacketing the outside of vessel 20. Vessel 20 could be jacketed with a prefabricated jacket such as plate coil commercially available from Thermon Corporation in San Marcos, Tex., or the jacket could be made of a welded halfpipe. The freeze time and melt time can be shortened by adding an additional coil or coils inside coil 40.

In a typical experimental purification run, industrial quality DMSO, (which typically does not meet U.S.P. specifications for pharmaceutical applications because it contains one or more impurities which result in excessive absorption of ultraviolet light at 275, 285, and 295 nanometers; or has excessive absorption of ultraviolet light at about 350 nanometers after the DMSO is treated with aqueous potassium hydroxide (as per U.S.P. specifications and test methods) is utilized as a starting liquid phase feed material. Approximately 8300 pounds of the industrial quality DMSO is loaded into vessel 10, and chilled, with the agitator running, while passing a 36° F., (2.2° C.) mixture of propylene glycol and water through two cooling coils having a surface area of approximately 132 square feet, for a period of approximately 7 hours. The temperature of the liquid DMSO during the time of DMSO crystallization is approximately 65–66° F., (18.5–18.8° C.). The flow of coolant is stopped, and uncrystallized DMSO mother liquor is transferred back to an industrial process for production of DMSO, using nitrogen pressure. Glycol is heated to approximately 105° F. (40.5° C.), and routed through the cooling coils, to melt the crystalline DMSO. The DMSO crystals can be, but need not be "sweated" by partial melting. The crystalline DMSO is melted to provide liquid DMSO over about 3 to 3.5 hours. The DMSO liquid is collected by transfer to another vessel via nitrogen pressure, and weighed. The typical yield of DMSO from the process is about 1250 pounds, or about 15% of the DMSO fed to Vessel 10. The DMSO produced by this method is typically sufficiently pure that it's ultraviolet absorption spectrum at 275, 285, 295 and/or 350nanometers meets or significantly exceeds U.S.P. specifications.

EXAMPLE 2

Industrial grade DMSO having an ultraviolet absorbance of about 0.23 absorbance units at 275 nanometers was blow-cased with dry nitrogen from a storage facility into a vessel similar to that of FIGS. 1–5, to a level of 86%, so as to totally cover the helical coil. The level of 86% corresponded to 8330 pounds of DMSO, at a temperature of 84.6° F. (29.2° C.). The agitator was started, and a mixture of water and propylene glycol was circulated through the upper and lower coils, and provided with cooling by a 12 ton (144,000 btu/hr, or 42 kilowatt) refrigeration unit. Initially the temperature of the water/propylene glycol mixture was about 55° F. (12.7° C.), but when the temperature of the liquid DMSO reached 65.3° F. (18.5° C.), and solid DMSO began to form on the coils, the temperature of the water/propylene glycol mixture had declined to about 33° F. (0.5° C.), and the temperature controller of the refrigeration unit began cycling.

After seven hours the agitator was stopped, and the liquid residue blow-cased into a receiving vessel. At this point, solid DMSO covered the cooling coils. The water/glycol mixture was then circulated and electrically heated, at temperatures not exceeding 105° F. (40.5° C.), averaging about 96° F. (35.5° C.). After 4 hours, the melted product was blow-cased to a product receiver, to produce about 1265 pounds of purified DMSO (about 15% of the initial charge of industrial grade DMSO). The purified product had an ultraviolet absorbance of 0.085 absorbance units at 275 nanometers. The ratio of the product's ultraviolet absorbance at 285 nanometers as compared to its absorbance at 275 nanometers was 0.35. The ratio of the product's ultraviolet absorbance at 295 nanometers as compared to its absorbance at 275 nanometers was 0.24.

Throughout this application, various publications are referenced. The disclosures of these publications in their entireties are hereby incorporated by reference into this application in order to more fully describe the state of the art to which this invention pertains.

In particular, the 1999 U.S. Pharmacopeia, USP 24, NF 19 (1999) contains the following description of the characteristics of U.S.P. grade dimethyl sulfoxide:

C2H6OS 78.13

Methane, sulfinyl[bis-.

Methyl sulfoxide [67–68–5].

Dimethyl Sulfoxide contains not less than 99.9 percent of $C_2H_6OS$.

Packaging and storage—Preserve in tight, light-resistant containers.

USP Reference standards (11)—USP Dimethyl Sulfoxide RS.

Identification A:

Infrared Absorption (197F). Potassium bromide plates being used.

B: Add 1.5 mL cautiously and dropwise to 2.5 mL of hydriodic acid in a test tube cooled in ice. Filter the mixture rapidly, and collect the precipitate. Dry the precipitate in vacuum: a deep violet, crystalline solid is obtained, and it is soluble in chloroform, yielding a red solution.

Specific gravity (841): between 1.095 and 1.097.

Congealing temperature (651): 18.3°, indicating not less than 99.9% of $C_2H_6OS$.

Refractive index (831): between 1.4755 and 1.4775.

Acidity—Dissolve 50.0 g in 100 mL of water, and add phenolphthalein TS. If the solution remains colorless, titrate with 0.01 N sodium hydroxide until a pink color appears: not more than 5.0 mL of 0.01 N sodium hydroxide is consumed.

Water, Method 1 (921): not more than 0.1%. [NOTE—Weigh and transfer the test specimen in an environment of low humidity to minimize absorption of atmospheric water.]

Ultraviolet absorbance—Maintain Dimethyl Sulfoxide in a water bath at a temperature of less than 20° [NOTE—Do not freeze.], and purge with dry nitrogen for 30 minutes. Record the ultraviolet absorption spectrum between 270 and 350 nm in a 1-cm cell, using water as the blank: the spectrum is smooth with no absorption maxima; the absorbance at 275 nm is not more than 0.20, and the absorbance ratios, $A_{285}/A_{275}$ and $A_{295}/A_{275}$ at the wavelengths indicated by the subscripts, are not more than 0.65 and 0.45, respectively.

Substances darkened by potassium hydroxide—Add 0.5 mL of water and 1.0 g of solid potassium hydroxide to 25 mL of Dimethyl Sulfoxide in a glass-stoppered, 50-mL flask. [NOTE—Use only solid potassium hydroxide that is white with no discoloration.] Insert the stopper, and heat in a steam cone for 20 minutes. Cool to room temperature: the absorbance of the solution at 350 nm. measured in a 2-cm cell, water being used as the blank, does not exceed 0.046.

Limit of dimethyl sulfone—

Resolution solution—Prepare a solution containing about 0.15 mg of dimethyl sulfone per mL and 0.1 mg of dibenzyl per mL in Dimethyl Sulfoxide.

Chromatographic system—The gas chromatograph is equipped with a flame-ionization detector and a suitable recorder, and contains a 1.5-m×3-mm column packed with 10% liquid phase G25 on packing S1A (see Chromatography (621)). The column is temperature-programmed at a rate of about 10° per minute from 100° to 170°, the injection port is maintained at a temperature of about 210°, and the detector block is maintained at a temperature of about 220°. Helium is used as the carrier gas, flowing at the rate of about 30 mL per minute. Chromatograph the Resolution solution, and record the peak responses as directed under Procedure: the column efficiency as determined from the dimethyl sulfoxide peak is not less than 1000 theoretical plates, and the resolution, R. between the dimethyl sulfone and dibenzyl peaks is not less than 5.0.

Procedure—By means of a suitable sampling valve or high-pressure microsyringe, inject about 1 μL of Dimethyl Sulfoxide, record the chromatograms, and measure the responses of the peaks: the response of any peak, other than that of dimethyl sulfoxide is not greater than 0.03% of the total of the responses of all of the peaks, and the total of the responses of all secondary peaks is not greater than 0.1% of the total of the responses of all of the peaks.

Limit of nonvolatile residue—Evaporate 50 g in a rotary evaporator at a pressure of about 30 mm of mercury at 95°. Wash the residue from the evaporator flask into a tared dish with several 25-mL portions of glass-distilled methanol, and evaporate on a hot plate in an exhaust hood: the weight of the residue does not exceed 5.0 mg.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for solidifying dimethylsulfoxide, comprising the steps of:
   a. providing a liquid phase comprising dimethylsulfoxide and one or more impurities,
   b. partially solidifying the liquid phase to form a mixture comprising solid dimethylsulfoxide and a liquid residue, wherein the liquid residue comprises liquid dimethylsulfoxide and at least a portion of the impurities, and
   c. substantially separating the solid dimethylsulfoxide from the liquid residue, wherein the process does not include the step of recycling the liquid residue such that the recycle results in subsequent treatment of the liquid residue by a solidification step b, and the dimethylsulfoxide separated in step c is not subsequently subjected to step b, and the ultraviolet absorbance of the separated dimethylsulfoxide at 275 nanometers is less than 0.20, and the ratio of the ultraviolet absorbance at 295 nanometers to the absorbance at 275 nanometers is less than 0.45, wherein the ultraviolet absorbance spectrum of the separated dimethylsulfoxide is measured as a liquid between 270 and 350 nanometers in a 1 centimeter cell at a temperature of less 20° C. using water as a blank.

2. The process of claim 1, further comprising the step of
   d. collecting the solid dimethylsulfoxide to provide purified dimethylsulfoxide.

3. The process of claim 2 consisting essentially of steps a, b, c, and d.

4. The process of claim 1, wherein the liquid phase comprises at least 90% dimethylsulfoxide by weight.

5. The process of claim 1, wherein the liquid phase is a grade of commercial dimethylsulfoxide other than U.S.P. grade dimethylsulfoxide.

6. The process of claim 1, wherein the ratio of the ultraviolet absorbance 285 nanometers to the absorbance at 275 nanometers is greater than 0.65.

7. The process of claim 1, wherein step b comprises cooling the liquid phase to a temperature effective to form solid dimethylsulfoxide.

8. The process of claim 1, wherein step b comprises agitating the liquid phase.

9. The process of claim 1, wherein step b comprises crystallizing.

10. The process of claim 1, wherein the solid dimethylsulfoxide formed comprises from about 1% to about 80% by weight of the liquid phase provided.

11. The process of claim 1, wherein a majority of the mixture of step b is the liquid residue.

12. The process of claim 1, wherein the solid dimethylsulfoxide formed comprises from about 7% to about 50% by weight of the liquid phase provided.

13. The process of claim 1, wherein the solid dimethylsulfoxide formed comprises from about 10% to about 30% by weight of the liquid phase provided.

14. The process of claim 1, wherein the separating comprises removing a major portion of the liquid residue from fluid contact with the solid dimethylsulfoxide, or removing a major portion of the solid dimethylsulfoxide from fluid contact with the major portion of the liquid residue.

15. The process of claim 1, further comprising the step of heating the solid dimethylsulfoxide to provide liquid dimethylsulfoxide.

16. The process of claim 1, further comprising heating the separated solid dimethylsulfoxide to form at least a portion of additional liquid residue, and substantially separating the additional liquid residue from the remaining solid dimethylsulfoxide.

17. The process of claim 2, wherein the purified dimethylsulfoxide has a purity suitable for use as a carrier vehicle for the administration of pharmaceutical agents to the bodies of living animals or humans.

18. The process of claim 2, wherein the purified dimethylsulfoxide;
  a) has a specific gravity between 1.095 and 1.097,
  b) has a congealing temperature equal to or greater than 18.30 indicating not less than 99.9% of $C_2H_6OS$,
  c) has a refractive index between 1.4755 and 1.4775,
  d) when 50.0 g of the purified dimethylsulfoxide is titrated for acidity in 100 mL of water with phenolphthalein, not more than 5.0 mL of 0.01 N sodium hydroxide is consumed,
  e) has a water content of not more than 0.1%,
  f) when 0.5 mL of water and 1.0 g of solid potassium hydroxide are added to 25 mL of the purified dimethylsulfoxide in a glass-stoppered 50-mL flask and heated in a steam cone for 20 minutes, the room temperature absorbance of the solution at 350 nm. measured in a 2-cm cell, water being used as the blank, does not exceed 0.046,
  g) nonvolatile residues do not exceed 5.0 milligrams when 50 grams of the purified dimethylsulfoxide is evaporated in a rotary evaporator at a pressure of about 30 mm of mercury at 95° C.,
  h) when the gas chromatogram of the purified dimethylsulfoxide is measured by the protocol described in the U.S.P. specifications for dimethylsulfoxide, the response of any peak other than that of dimethylsulfoxide is not greater than 0.03% of the total of the responses of all of the peaks, and the total of the responses of all secondary peaks is not greater than 0.1% of the total of the responses of all of the peaks.

19. The process of claim 2, wherein the ultraviolet absorbance of the purified dimethylsulfoxide at 275 nanometers is less than 0.20, and the ratio of the ultraviolet absorbance at 285 nanometers to the absorbance at 275 nanometers is less than 0.65, and the ratio of the ultraviolet absorbance at 295 nanometers to the absorbance at 275 nanometers is less than 0.45, wherein the ultraviolet absorbance spectrum of the purified dimethylsulfoxide is measured as a liquid between 270 and 350 nanometers in a 1 centimeter cell at a temperature of less 20° C. using water as a blank.

20. The process of claim 1, wherein the liquid residue is reclaimed by addition to a process for the production of dimethylsulfoxide, which process does not include the step of solidifying dimethylsulfoxide to produce purified dimethylsulfoxide.

21. The process of claim 20, wherein the process for the production of dimethylsulfoxide does not produce U.S.P. grade dimethylsulfoxide.

22. The process of claim 1, wherein the liquid residue is reclaimed by distillation.

23. The process of claim 1, wherein the liquid residue from step b is discarded, sold, or used for non-U.S.P. applications.

24. The process of claim 1, wherein step b occurs in a solidification apparatus.

25. The process of claim 24, wherein the solidification apparatus is a melt-crystallization apparatus.

26. A process for purifying dimethylsulfoxide by melt crystallization, comprising the steps of:
  a. providing a liquid phase comprising greater than about 90% by weight of liquid dimethylsulfoxide, and one or more impurities,
  b. agitating and cooling the liquid phase to approach a temperature of about 18.5° C. or lower, to form a mixture of solid dimethylsulfoxide and a liquid residue, the liquid residue comprising liquid dimethylsulfoxide and a substantial portion of the impurities,
  c. substantially separating the solid dimethylsulfoxide from the liquid residue, and
  d. melting the solid dimethylsulfoxide to provide purified dimethylsulfoxide, wherein:
    i. the liquid residue is not recycled to the extent it results in treatment of the liquid residue by step b,
    ii. the purified dimethylsulfoxide is not subsequently subjected to steps a, b, and c, and
    iii. the ultraviolet absorbance of the purified dimethylsulfoxide at 275 nanometers is less than 0.20, and the ratio of the ultraviolet absorbance at 285 nanometers to the absorbance at 275 nanometers is less than 0.65, and the ratio of the ultraviolet absorbance at 295 nanometers to the absorbance at 275 nanometers is less than 0.45, wherein the ultraviolet absorbance spectrum of the purified dimethylsulfoxide is measured as a liquid between 270 and 350 nanometers in a 1 centimeter cell at a temperature of less 20° C. using water as a blank.

* * * * *